US009308351B2

United States Patent
Honig

(10) Patent No.: US 9,308,351 B2
(45) Date of Patent: *Apr. 12, 2016

(54) TUNNELED CATHETER WITH HEMOSTASIS MECHANISM

(71) Applicant: SMH Device Corp., New York, NY (US)

(72) Inventor: Shaun M. Honig, New York, NY (US)

(73) Assignee: SMH Device Corp., New York, NY (US)

(*) Notice: Subject to any disclaimer, the term of this patent is extended or adjusted under 35 U.S.C. 154(b) by 25 days.

This patent is subject to a terminal disclaimer.

(21) Appl. No.: 14/242,996

(22) Filed: Apr. 2, 2014

(65) Prior Publication Data

US 2014/0358076 A1   Dec. 4, 2014

Related U.S. Application Data

(63) Continuation-in-part of application No. 13/903,022, filed on May 28, 2013, now Pat. No. 9,067,043.

(51) Int. Cl.
   *A61M 25/01*  (2006.01)
   *A61M 1/36*  (2006.01)
   *A61M 25/10*  (2013.01)
   (Continued)

(52) U.S. Cl.
   CPC ....... *A61M 25/0194* (2013.01); *A61M 25/1011* (2013.01); *A61M 1/3661* (2014.02); *A61M 25/0017* (2013.01); *A61M 25/10185* (2013.11);
   (Continued)

(58) Field of Classification Search
   CPC .............. A61M 25/04; A61M 2039/0261; A61M 2025/006; A61M 25/0017; A61M 25/02
   See application file for complete search history.

(56) References Cited

U.S. PATENT DOCUMENTS

| 2,927,584 A | 3/1960 | Wallace |
| 3,543,759 A | 12/1970 | McWhorter |

(Continued)

FOREIGN PATENT DOCUMENTS

WO   9727897 A1   8/1997

OTHER PUBLICATIONS

Marcie Gruchevsky, et al., Rapid Hemostasis Leading to Early Ambulation in Diagnostic Cardiac and Peripheral Angiography Patients Using V+Pad in Conjunc, Cath Lab Digest, Jun. 2006, vol. 14 Issue 6.

(Continued)

*Primary Examiner* — Kevin C Sirmons
*Assistant Examiner* — William Carpenter
(74) *Attorney, Agent, or Firm* — Wiggin and Dana LLP; Gregory S. Rosenblatt

(57) ABSTRACT

A hemostasis component for an invasive medical device has an inflatable cylinder affixed to the medical device at a location aligned with an ingress point of a patient. An inflation source is in fluid communication with the inflatable cylinder and a flow control valve that is effective to regulate the flow of fluid from the inflation source to the inflatable cylinder is provided. The flexible cylinder is located on the proximal end of a tunneling catheter, where it exits the skin. A thin tube is provided to inflate the flexible cylinder. In the event of bleeding, the flexible cylinder is inflated for as long as is needed to achieve hemostasis, without having to place sutures. Inflation is a simple procedure that can be done by the patient, as opposed to having to place a suture, which must be performed by a physician or a physician's delegate, under sterile conditions.

5 Claims, 6 Drawing Sheets

(51) Int. Cl.
*A61M 39/02* (2006.01)
*A61M 25/00* (2006.01)

(52) U.S. Cl.
CPC .. *A61M 2025/105* (2013.01); *A61M 2039/0258* (2013.01); *A61M 2039/0261* (2013.01)

(56) References Cited

U.S. PATENT DOCUMENTS

| | | | |
|---|---|---|---|
| 3,699,956 A | 10/1972 | Kitrilakis et al. | |
| 3,788,326 A | 1/1974 | Jacobs | |
| 3,915,171 A | 10/1975 | Shermeta | |
| 4,184,497 A | 1/1980 | Kolff et al. | |
| 4,266,999 A | 5/1981 | Baier | |
| 4,278,092 A | 7/1981 | Borsanyi et al. | |
| 4,496,349 A | 1/1985 | Cosentino | |
| 4,676,782 A * | 6/1987 | Yamamoto et al. | 604/175 |
| 4,751,924 A | 6/1988 | Hammerschmidt et al. | |
| 4,771,777 A * | 9/1988 | Horzewski | A61M 25/1011 604/101.05 |
| 4,772,269 A | 9/1988 | Twardowski et al. | |
| 4,832,688 A | 5/1989 | Sagae et al. | |
| 4,863,426 A | 9/1989 | Ferragamo et al. | |
| 5,049,140 A | 9/1991 | Brenner et al. | |
| 5,053,023 A | 10/1991 | Martin | |
| 5,057,075 A | 10/1991 | Moncrief et al. | |
| 5,135,474 A * | 8/1992 | Swan | A61M 25/1011 604/101.05 |
| 5,190,046 A | 3/1993 | Shturman | |
| 5,308,338 A | 5/1994 | Helfrich | |
| 5,315,992 A | 5/1994 | Dalton | |
| 5,507,284 A | 4/1996 | Daneshvar | |
| 5,540,715 A | 7/1996 | Katsaros et al. | |
| 5,645,556 A * | 7/1997 | Yoon | 606/185 |
| 5,645,566 A * | 7/1997 | Brenneman et al. | 606/213 |
| 5,653,230 A | 8/1997 | Ciaglia et al. | |
| 5,718,692 A | 2/1998 | Schon et al. | |
| 5,776,111 A | 7/1998 | Tesio | |
| 5,830,184 A | 11/1998 | Basta | |
| 5,904,147 A | 5/1999 | Conlan et al. | |
| 5,947,939 A * | 9/1999 | Mortier | A61M 25/005 600/435 |
| 5,947,953 A | 9/1999 | Ash et al. | |
| 5,984,896 A | 11/1999 | Boyd | |
| 5,989,213 A | 11/1999 | Maginot | |
| 5,994,732 A * | 11/1999 | Ajika | H01L 27/115 257/315 |
| 6,007,522 A | 12/1999 | Agro et al. | |
| 6,033,382 A | 3/2000 | Basta | |
| 6,071,300 A | 6/2000 | Brenneman et al. | |
| 6,119,697 A * | 9/2000 | Engel | A61F 2/0027 128/885 |
| 6,156,016 A | 12/2000 | Maginot | |
| 6,475,207 B1 | 11/2002 | Maginot et al. | |
| 6,494,848 B1 | 12/2002 | Sommercorn et al. | |
| 6,939,328 B2 | 9/2005 | Raulerson | |
| 7,625,352 B1 * | 12/2009 | Ashby | A61B 17/0057 604/15 |
| 7,753,889 B2 | 7/2010 | Rosenberg | |
| 7,798,998 B2 | 9/2010 | Thompson et al. | |
| 8,100,863 B2 | 1/2012 | Moehle et al. | |
| 8,827,985 B1 * | 9/2014 | Barnett | 604/544 |
| 2005/0209583 A1 | 9/2005 | Powers et al. | |
| 2005/0228443 A1 | 10/2005 | Yassinzadeh | |
| 2006/0200111 A1 | 9/2006 | Moehle et al. | |
| 2007/0185510 A1 * | 8/2007 | Tran | 606/167 |
| 2008/0045894 A1 | 2/2008 | Perchik et al. | |
| 2009/0209950 A1 | 8/2009 | Starksen | |

OTHER PUBLICATIONS

Grant W. Berry, et al., Topical Hemostatic Agents, Medscape, May 13, 2011.

* cited by examiner

TUNNELED CATHETER WITH HEMOSTASIS MECHANISM

CROSS REFERENCE TO RELATED APPLICATION(S)

This patent application is a continuation in part of U.S. Pat. No. 9,067,043 that issued on Jun. 30, 2015 and is titled "Tunneled Catheter with Hemostasis Mechanism." The disclosure of U.S. Pat. No. 9,067,043 is incorporated by reference herein in its entirety.

U.S. GOVERNMENT RIGHTS

N.A.

BACKGROUND

1. Field

This disclosure relates to medical devices having a hemostasis component. More particularly, an expandable sleeve on the proximate end of a catheter is effective to stanch blood flow.

2. Description of the Related Art

Patients with end stage renal disease (ESRD) often require long term hemodialysis which is performed using a surgically placed AV fistula, a connection between a vein and an artery. While a patient is waiting for fistula surgery, or if the fistula is not working properly, dialysis can be performed via a tunneled catheter, also referred to as a PERMCATH® catheter (Trademark of Covidien AG Corporation, Am Rheinfall, Switzerland).

The catheter is a large bore catheter (15-16 French size) which is tunneled from the subcutaneous tissues of the chest wall, and then inserted into the internal jugular vein (or other large vein) using interventional radiology techniques. Exemplary is the Quinton™ Permcath™ Dual Lumen Catheter (trademark of Covidien, Mansfield, Mass.) that provides blood flow rates of 350-400 mL/min and maintains low arterial and venous pressures. The catheter is made of a soft, silicone material and is designed with a staggered tip to provide a 2.5 cm separation between the arterial lumen and venous tip. The catheter is provided in a variety of insertion lengths to accommodate different patient anatomies and physician insertion practices.

The process of tunneling the catheter involves attaching the catheter to a long metal tunneling device which bores through the subcutaneous tissues. The tunneling process is traumatic as small blood vessels in the subcutaneous tissues are torn by the tunneling device causing bleeding out of the tunnel track. This is even more problematic in patients with ESRD, as their blood does not clot as well due to problems with platelet function, which is necessary to adequately clot the blood. Physicians are often called to deal with bleeding from the permcath site. Medical intervention can be time consuming, as it requires anything from holding pressure to putting in sutures in order to stop the bleeding. Sutures must be removed at some point because skin damage can occur if the sutures remain for an extended period of time.

Devices for promoting hemostasis in a blood vessel puncture are disclosed in U.S. Pat. No. 5,904,147 to Conlan et al. and in U.S. Pat. No. 6,071,300 to Brenneman et al. Both U.S. Pat. No. 5,904,147 and U.S. Pat. No. 6,071,300 are incorporated by reference herein in their entireties.

Accordingly, there remains a need for an improved tunneling catheter for hemodialysis and others functions that has an improved hemostasis component.

BRIEF SUMMARY

It is an object of certain embodiments disclosed herein to provide a balloon, or other inflatable member, located on the proximal end of the catheter for long term hemodialysis, where it exits the skin. A thin tube is provided to inflate the balloon. In the event of bleeding, the balloon can be inflated for as long as is needed to achieve hemostasis, without having to place sutures. Inflating the balloon is a very simple procedure that can even be done by the patient themselves, as opposed to having the place a suture, which must be performed by a physician or a physician's delegate such as a physician's assistant, under sterile conditions.

The details of one or more embodiments of the invention are set forth in the accompanying drawings and the description below. Other features, objects and advantages of the invention will be apparent from the description and drawings, and from the claims.

BRIEF DESCRIPTION OF THE DRAWINGS

Like reference numbers and designations in the various drawings indicated like elements.

DETAILED DESCRIPTION

As used herein, an "invasive medical device" is one that is intended to puncture the skin of a subject when used its intended manner. "Subject" refers to any mammal, human or non-human and the invasive devises are equally applicable to medical and veterinary procedures.

Figure 1:
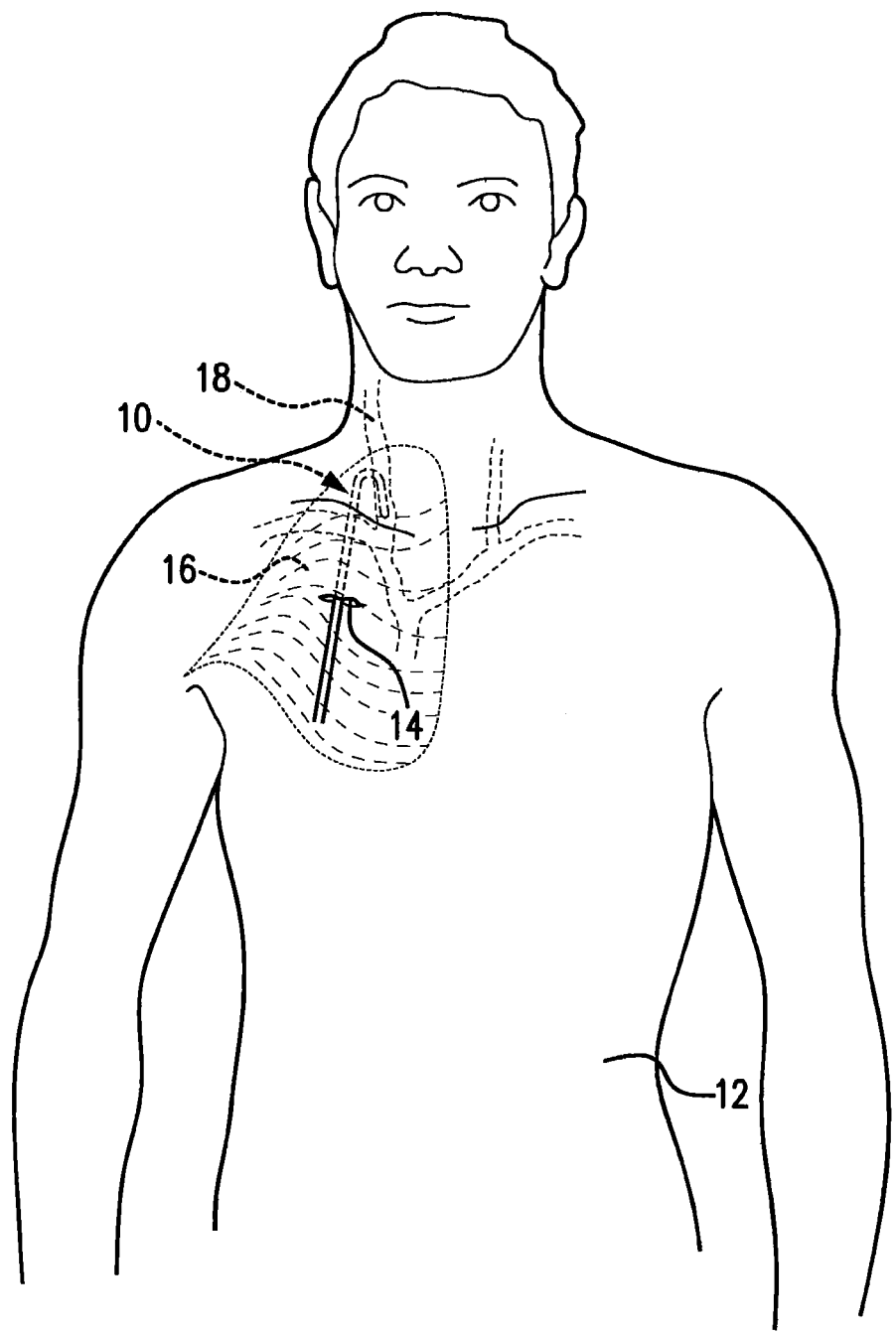
FIG. 1 illustrates a catheter for long term hemodialysis ingress into subcutaneous tissues of a chest wall as known from the prior art.
Figure 2:
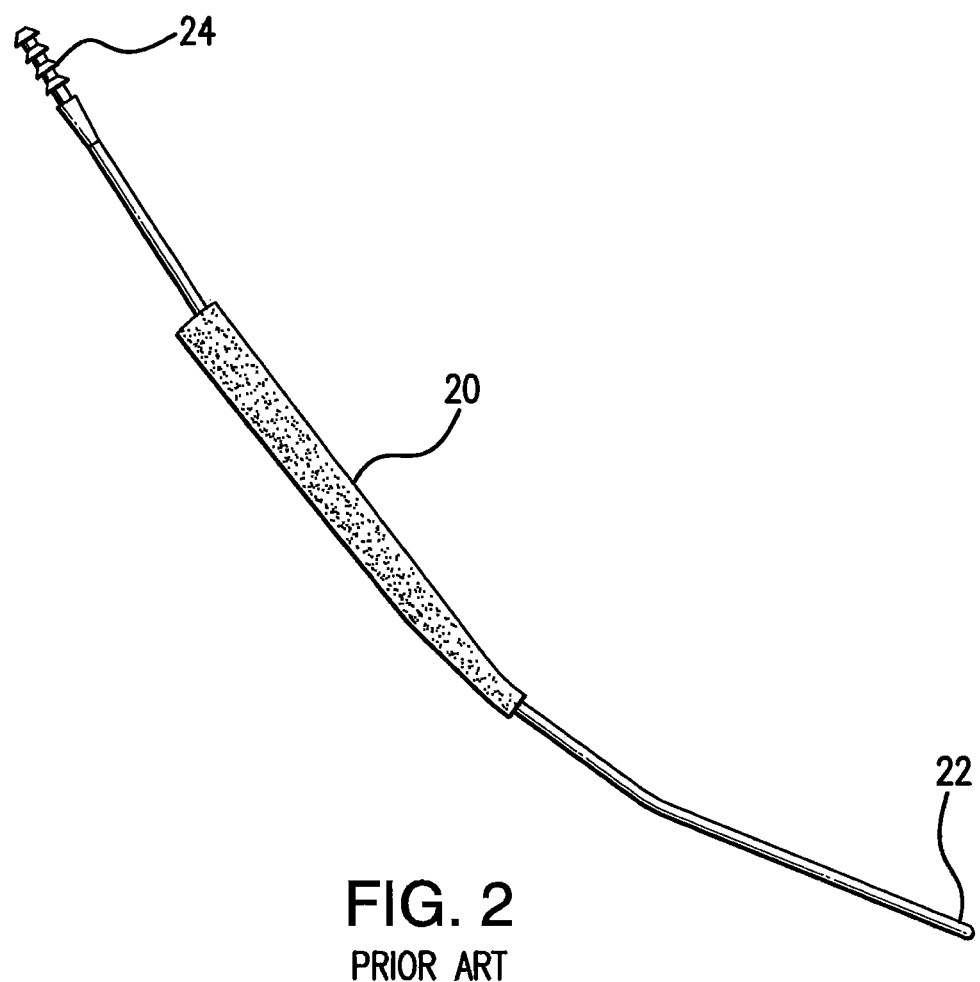
FIG. 2 illustrates a tunneling device for use with a catheter for long term hemodialysis as known from the prior art.
Figure 3:
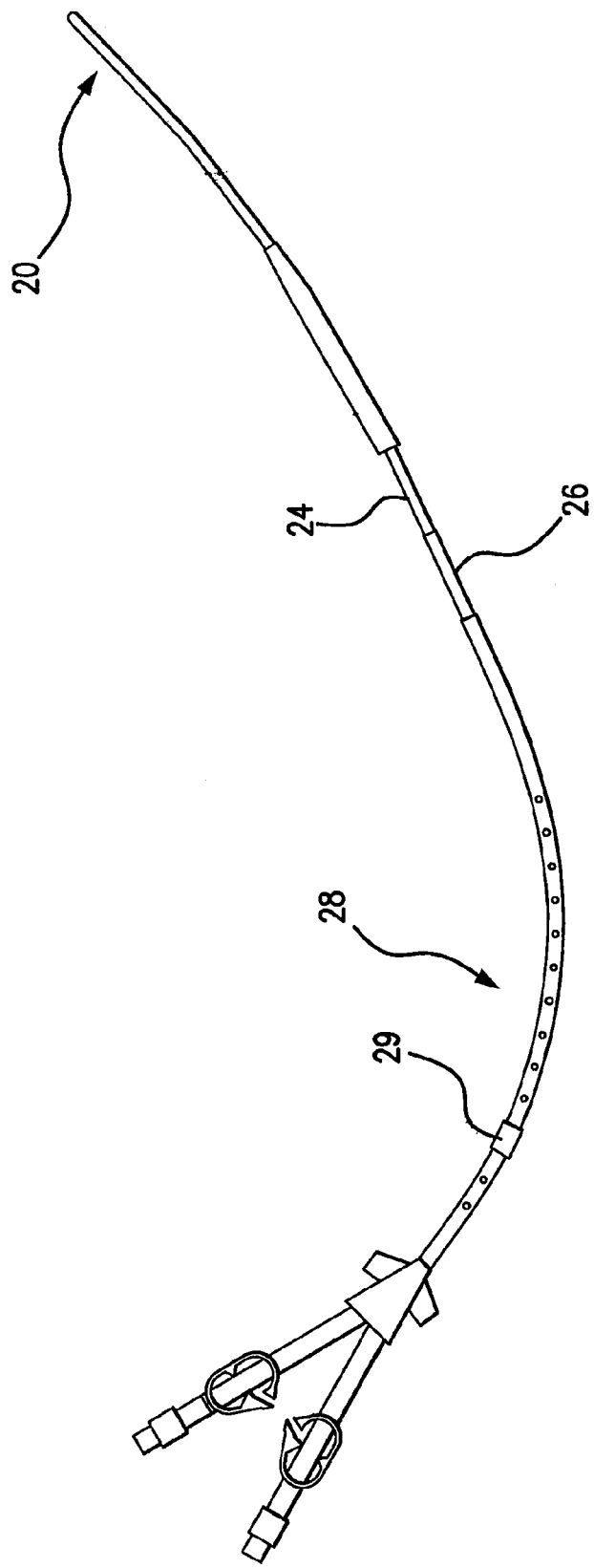
FIG. 3 illustrates the tunneling device of FIG. 2 attached to a catheter for long term hemodialysis as known from the prior art.

FIG. 1 illustrates a tunneled catheter 10 inserted into a patient 12 with ingress 14 being through the chest wall. The tunneled catheter 10 is tunneled through subcutaneous tissue 16 of the chest wall for insertion into a jugular vein 18. FIG. 2 shows a tunneling device 20 for use with a tunneled catheter. The tunneling device 20 is fanned from a hard biocompatible material, such as stainless steel, and has a distal end 22 that comes to a point effective for boring through subcutaneous tissue. An opposing proximal end 24 contains features, such as threads, for engagement with the tunneled catheter. FIG. 3 shows the proximal end 24 of the tunneling device 20 fastened to a distal end 26 of tunneled catheter 28. An anchoring cuff 29 is disposed at a location, which on proper insertion, will be in the subcutaneous tissue, close to the ingress. The anchoring cuff 29 both fixes the positioning of the tunneled catheter 28 and functions as a bacteria blocker to prevent bacteria from entering the patient 12 through the ingress 14.

Figure 4:
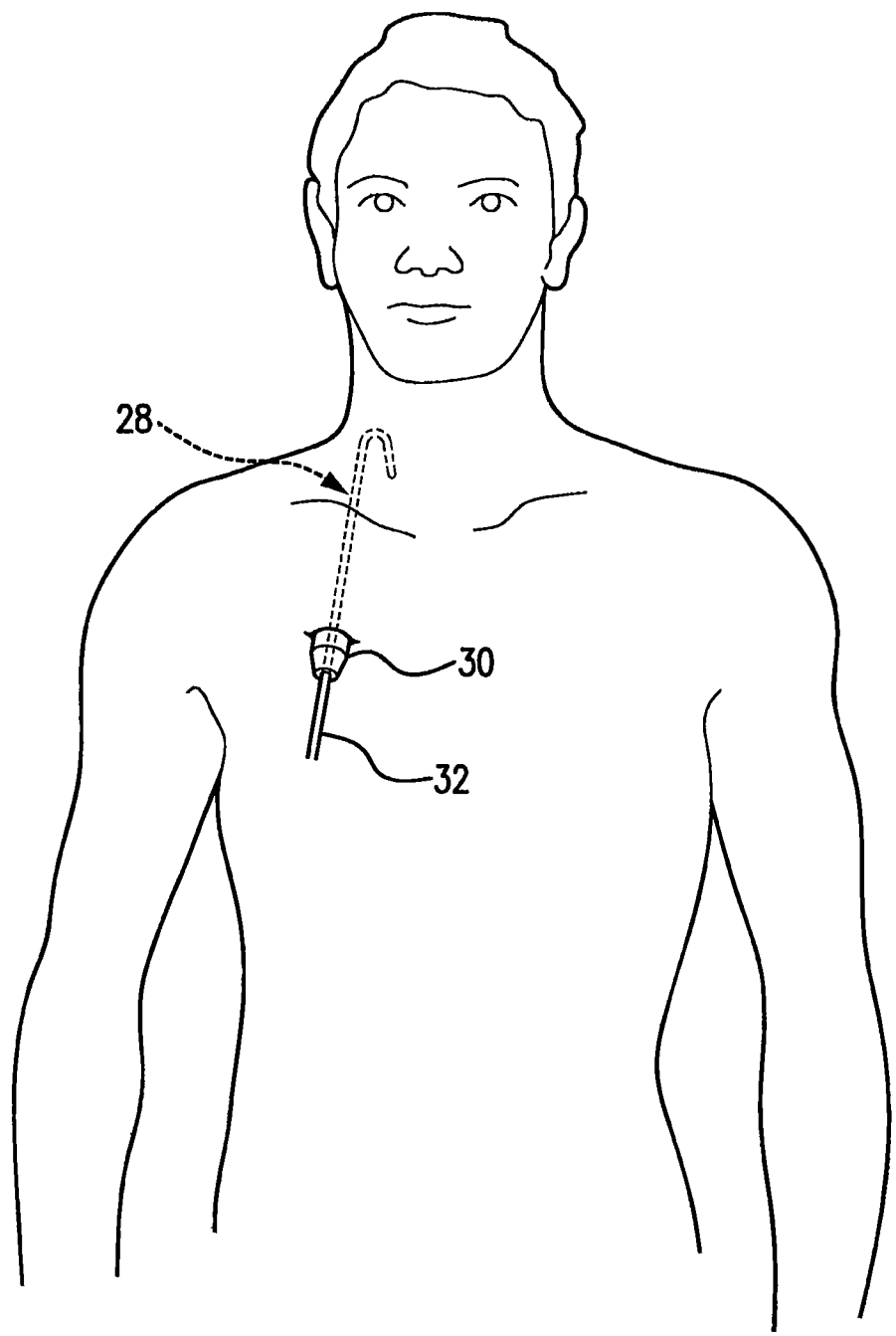
FIG. 4 illustrates a catheter for long term hemodialysis ingress into subcutaneous tissues of a chest wall where the catheter for long term hemodialysis includes a hemostasis component.

Referring back to FIG. 1, the tunneling process is traumatic and small blood vessels in the subcutaneous tissue 16 are torn causing bleeding that flows along the tunnel track and exits the patient 12 at ingress 14. With reference to FIG. 4, a hemostasis component 30 is affixed to a proximal end 32 of the tunneled catheter 28. In the event of bleeding, the hemostasis component 30 is inflated for as long as is needed to achieve hemostasis, without having to place sutures.

Figure 5:
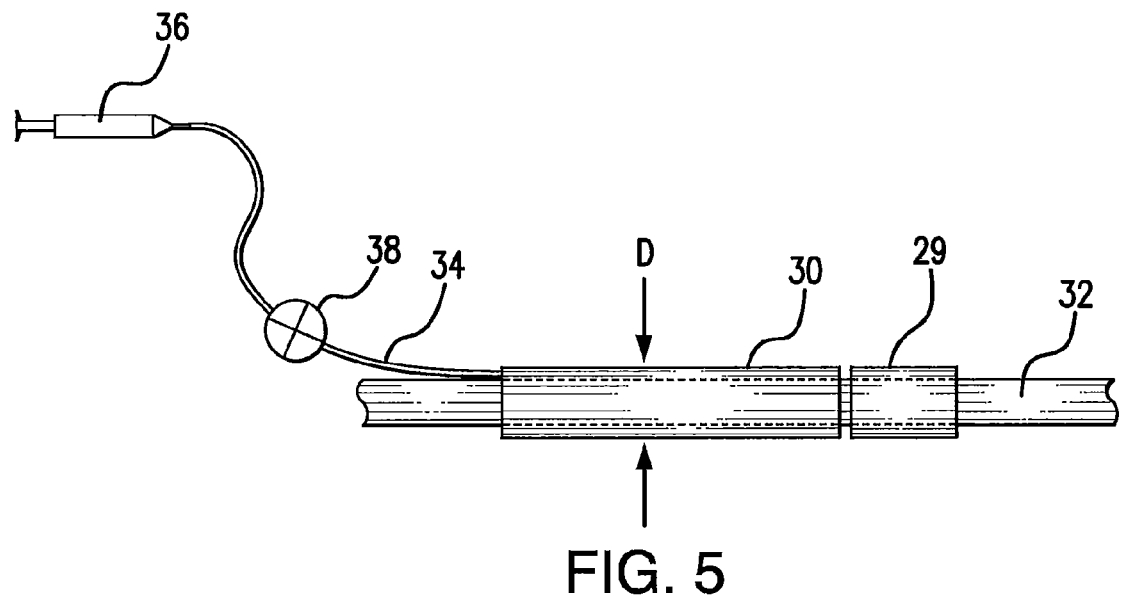
FIG. 5 illustrates a portion of a first embodiment the catheter for long term hemodialysis of FIG. 4 prior to deployment of the hemostasis component.

FIG. 5 illustrates the hemostasis component 30 affixed to the proximal end 32 of a tunneled catheter adjacent anchoring cuff 29, in accordance with a first embodiment. The diameter, D, of the hemostasis component is sufficient small to permit insertion into the ingress (14 of FIG. 1). The hemostasis component 30 typically has a hollow cylindrical shape and is formed from biocompatible flexible material such as silicone, PET (polyethylene terephthalate) or nylon. An inflation tube 34 is in fluid communication with the interior of the hemostasis component 30. The inflation tube is also in fluid communication with an inflation source 36, such as a syringe. A flow control valve 38 regulates the flow of fluid from the inflation source 36 to the hemostasis components 30 and out from the hemostasis components when bleeding has stopped, typically in about 15 minutes. As an inflated hemostasis component may compress the proximal end 32 of the catheter reducing its inside diameter, the hemostasis component is preferably deflated prior to commencing a flow of fluids through the catheter.

Figure 6:
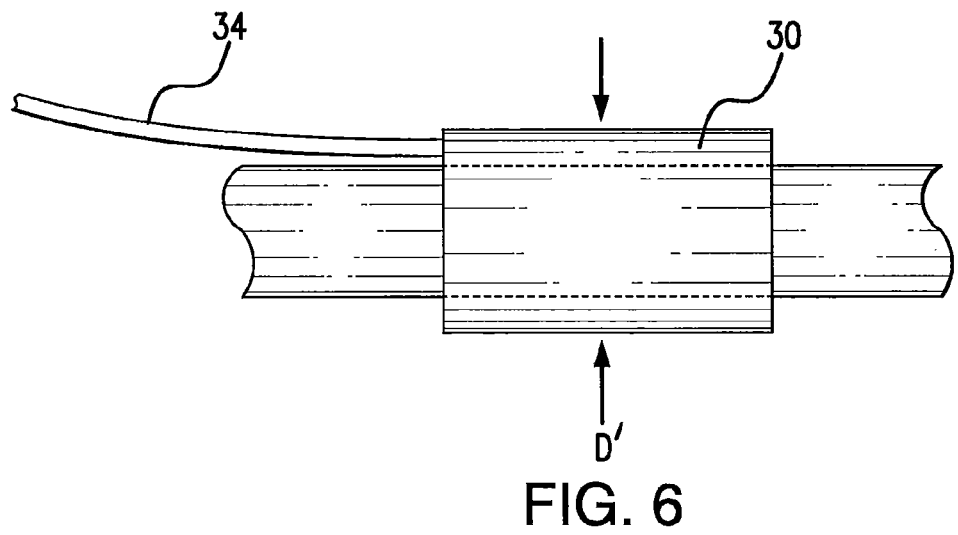
FIG. 6 illustrates the portion of the catheter for long term hemodialysis of FIG. 5 subsequent to deployment of the hemostasis component.

Referring to FIG. 6, in the event there is bleeding at the ingress (14 in FIG. 1), a fluid, such as air, purified water or a saline solution, is conducted via inflation tube 34 to the hemostasis component 30 inflating the hemostasis component to a diameter, D'. D' is slightly larger than the diameter of the ingress to apply a positive pressure against the subcutaneous tissue immediately below the ingress to thereby stanch the bleeding.

Figure 7:
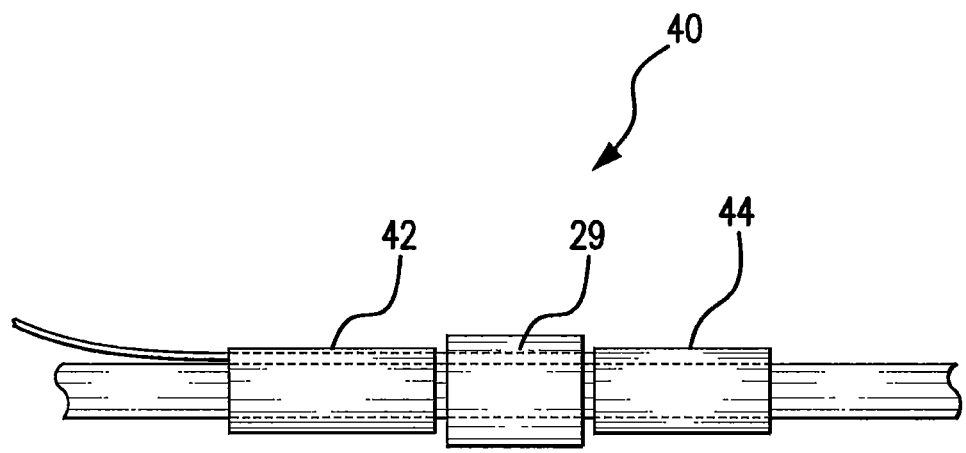
FIG. 7 illustrates a portion of a second embodiment the catheter for long tern hemodialysis of FIG. 4 prior to deployment of the hemostasis component.
Figure 8:
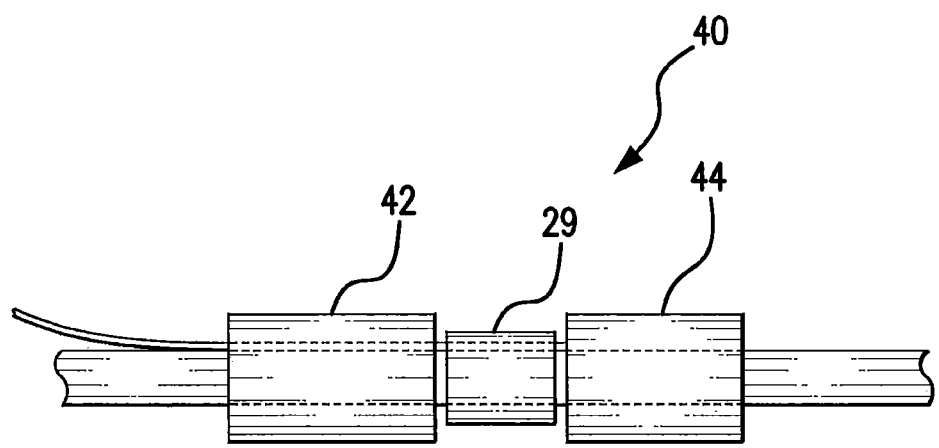
FIG. 8 illustrates the portion of the catheter for long term hemodialysis of FIG. 7 subsequent to deployment of the hemostasis component.

Referring to FIGS. 7 (uninflated) and 8 (inflated), in accordance with a second embodiment, the hemostasis component 40 may be an inflatable cylinder located on either side of the anchoring cuff 29, or be a double cylinder 42, 44 positioned on either side of the anchoring cuff 29. Alternatively, the hemostasis component may be an expandable foam material or a coating of a drug that promotes hemostasis, such as thrombin. Other hemostasis promoting materials that may be incorporated in to the expandable foam include D-glucosamine-enriched fibers, bone wax (typically a mixture of beeswax, paraffin, isopropyl palmitate and a wax-softening agent), ostene (mixture of water-soluble alkylene oxide copolymers, Baxter Healthcare Corporation, Deerfield, IL), acrylics (such as an intermediate chain cyanoacrylate, butyl-2-cyanoacrylate, a longer chain cyanoacrylate octyl-2-cyanolate, and octyl acrylate), a ferric subsulfate solution, silver nitrate, aluminum chloride, mineral zeolite, gelatin, microfibrillar collagen, poly-N-acetyl glucosamine, kaolinite, Pro QR Powder (a mixture of potassium ferrate salt and a hydrophilic polymer available from Biolife, Sarasota, FL), epinephrine and fibrin sealant.

With reference back to FIG. 5, the inflation source 36 may be charged with a fluid containing one or more of the hemostasis promoting materials and the hemostasis component 30 may be porous to that fluid such that when the hemostasis component 30 is inflated, an exterior surface of that hemostasis component becomes coated with the hemostasis promoting material.

One or more embodiments of the present invention have been described. Nevertheless, it will be understood that various modifications may be made without departing from the spirit and broad scope of the invention. Accordingly, other embodiments are within the scope of the following claims.

What is claimed is:

1. A tunneled catheter comprising:
a catheter for long term hemodialysis having a distal end and a proximal end, wherein an anchoring cuff and a hemostasis component are disposed on the proximal end;
a tunneling device affixed to a distal end of the catheter;
the hemostasis component is an inflatable, double cylinder disposed proximally and distally of the anchoring cuff and both cylinders are inflatable by a same inflation tube; and
said inflation tube connecting an inflation source with said hemostasis component and a flow control valve regulates flow of a fluid from said inflation source to said hemostasis component.

2. The tunneled catheter of claim 1 wherein a chemical compound is in a mixture with said fluid and said hemostasis component is porous to said mixture.

3. The tunneled catheter of claim 2 wherein said chemical compound is selected from the group consisting of thrombin, D-glucosamine-enriched fibers, bone wax, ostene, a ferric subsulfate solution, silver nitrate, aluminum chloride, mineral zeolite, gelatin, microfibrillar collagen, poly-N-acetyl glucosamine, kaolinite, a mixture of potassium ferrate salt and a hydrophilic polymer, epinephrine and fibrin sealant.

4. The tunneled catheter of claim 3 wherein said hemostasis component is formed from a flexible biocompatible material.

5. The tunneled catheter of claim 4 wherein said flexible biocompatible material is selected from the group consisting of silicone, polyethylene terephthalate and nylon.

* * * * *